United States Patent [19]
Flagan et al.

[11] Patent Number: 5,596,136
[45] Date of Patent: Jan. 21, 1997

[54] RADIAL DIFFERENTIAL MOBILITY ANALYZER

[75] Inventors: Richard C. Flagan; Shou-Hua Zhang, both of Pasadena, Calif.

[73] Assignee: California Institute of Technology, Pasadena, Calif.

[21] Appl. No.: 508,311

[22] Filed: Jul. 27, 1995

[51] Int. Cl.[6] .................................................. G01N 27/60
[52] U.S. Cl. .................................. 73/28.04; 324/452
[58] Field of Search ........................... 73/865.5, 863.21, 73/28.01, 28.02, 28.04; 55/270; 356/440; 324/452, 464; 250/294

[56] References Cited

U.S. PATENT DOCUMENTS 5,117,190  5/1992  Pourprix ........................... 324/452
5,150,037  9/1992  Kouzuki ........................... 73/865.5

Primary Examiner—Robert Raevis
Attorney, Agent, or Firm—Michaelson & Wallace

[57] ABSTRACT

The present invention provides a differential mobility analyzer for the classification of aerosols, comprising a chamber having two generally parallel faces and means to confine gases in the chamber, one of the faces having a generally arcuate, annular sheath air channel having an axis of symmetry, other of the faces having a generally arcuate, annular aerosol channel having an axis of symmetry generally coincident with the axis of symmetry of the sheath air channel, a first one of the faces having a sample flow aperture generally aligned with the axis of symmetry of the sheath air channel, a second one of the faces having an excess flow aperture generally aligned with the axis of symmetry of the sheath air channel, and means for maintaining an electric potential difference between the faces.

32 Claims, 3 Drawing Sheets

{ 5,596,136 }

RADIAL DIFFERENTIAL MOBILITY ANALYZER

ORIGIN OF THE INVENTION

The United States Government has certain rights in this invention pursuant to Grant No. CTS9113191 awarded by the National Science Foundation.

BACKGROUND OF THE INVENTION

1. Technical Field

The present invention relates to devices used for the measurement of aerosol particles and, in particular, the size distribution and mobility of such particles.

2. Background Art

Differential mobility analyzers (DMA) have been used to classify and analyze aerosol particles. The measurement of such particles has substantial commercial importance, including the analysis of atmospheric pollutants, the characterization of contaminants in laboratories and controlled production environments, the calibration of aerosol instruments, and the separation of particle sizes to produce monosized particles. Aerosol particles may be composed of various organic and inorganic materials and vary in size from one nanometer to approximately 100 microns.

The classification of aerosol particles by a DMA is based on the property that such particles carry electrical charge. An electrostatic field is applied by the DMA and positive and negative charges migrate or deflect under the field toward the electrode with an opposite electric charge. One common DMA employs coaxial cylinders as electrodes in a two-inlet, two outlet flow configuration (Hewitt, 1957). Although a commercialized version has been widely used for the generation of monodisperse particles and the size classification of polydisperse aerosols, the high cost of precision machining to produce the cylinders is a significant disadvantage.

One approach to reducing the cost of the DMA is the use of a circular configuration for the electrodes, such as the designs disclosed in the cumulative mobility analyzer of Hurd and Mullins (1962) and the mobility classifier of U.S. Pat. No. 5,117,190 (Pourprix). These devices have reduced the cost, size and weight of such analyzers, but continue to exhibit other drawbacks. For example, in the DMA disclosed by Pourprix, the analyzer extracts an aerosol sample in such a manner that the number of particles detected for specific test conditions (such as flow rate and applied voltage) will be produced by aerosol particles with a wide size distribution rather than a narrow one, which can result in an inaccurate size distribution. As shown in FIG. 8 of U.S. Pat. No. 5,117,190, the aerosol sample is extracted through an annular slot 76 and into a cylindrical case 82, before the sample is extracted through a tube 84 for analysis. The collection of particles in the case 82 results mixing or diffusion of particle sizes produced during one set of test conditions with those of a previous set of test conditions, which may be referred to as a "time hysteresis effect." This time hysteresis effect reduces the resolution of the DMA when the applied voltage is varied either continuously or incrementally by rapidly stepping through values.

In addition, the DMA disclosed in the Pourprix patent experiences difficulty in measuring ultrafine aerosol particles, for example less than 10 nm. This is primarily due to aerosol particle losses in the entrance slots, which produce a radial flow of aerosol that flows in a centripetal manner toward the center of the circular electrodes.

SUMMARY OF THE INVENTION

The radial differential mobility analyzer ("RDMA") according to the present invention retains the size and weight advantages of previous RDMA devices, while reducing the manufacturing cost and overcoming significant disadvantages. For example, the RDMA disclosed herein overcomes the time hysterisis effect by withdrawing the aerosol sample at the center of the circular electrode, thus avoiding any mixing or diffusion of particle sizes from previous test conditions. Further, the RDMA of the invention reduces the loss of small aerosol particles at the entrance to the device by introducing the sample aerosol in a tangential manner. Finally, the present RDMA further reduces manufacturing costs over previous RDMA devices, such as the one disclosed by Pourprix, because the RDMA according to the invention does not use a second cavity for collection of aerosol particles to be extracted for analysis.

The invention is embodied in a differential mobility analyzer for the classification of aerosols, including a chamber having two generally parallel faces and means to confine gases in the chamber; one of the faces having a generally arcuate, annular sheath air channel, having an axis of symmetry; another of the faces having a generally arcuate, annular aerosol channel having an axis of symmetry generally coincident with the axis of symmetry; a first one of the faces having a sample flow aperture generally aligned with the axis of symmetry; a second one of the faces having an excess flow aperture generally aligned with the axis of symmetry; and means for maintaining an electric potential difference between the faces.

DETAILED DESCRIPTION OF THE PREFERRED EMBODIMENT

Figure 1:
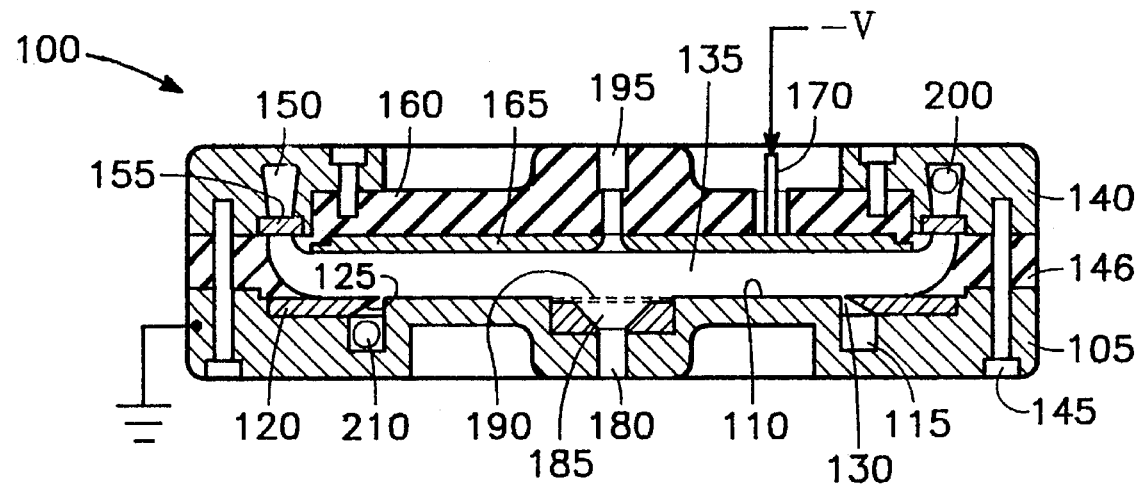
FIG. 1 is a cross section view of the analyzer of the present invention.

A differential mobility analyzer ("RDMA") 100 of the present invention is shown in FIG. 1. A portion of a housing 105 forms a first circular electrode 110. An annular sample channel 115 is formed in the body of housing 105 at the periphery of electrode 110, which sample channel 115 carries the aerosol to be analyzed. An annular ring 120 with a sharp inner edge 125 is mounted over sample channel 115, forming an aerosol inlet gap 130 through which the aerosol to be analyzed flows into test chamber 135.

An annular sealing cap 140 is affixed to housing 105 with fasteners 145 and an annular insulating ring 146. An annular sheath air channel 150 is formed in the cap 140, with an inner diameter greater than the outer diameter of sample channel 115. The sheath air channel 150 has an axis of symmetry perpendicular to the plane in which it is located, which axis is generally coincident with the axis of symmetry of the sample channel 115. An annular insert 155 covers the top of sheath air channel 150. An insulating disk 160 is mounted at the inner edge of annular sealing cap 140 and a second circular electrode 165 is affixed to the bottom of insulating disk 160, facing the test chamber 135, and located coaxially with the first circular electrode 110. An electric potential difference between the electrodes is applied by a voltage connector 170 conductively affixed to the second circular electrode 165. Any other suitable means to impart an electric potential difference may be employed, such as a wire attached to the second circular electrode 165.

An excess flow outlet 180 is provided along the axis of symmetry of the sample channel 115, which outlet is provided with a conical outlet port 185 facing the test chamber 135. A circular conducting screen 190 covers the conical outlet port 185. A sample flow outlet 195 is provided along the axis of symmetry of the sheath air channel 150.

Figure 2:
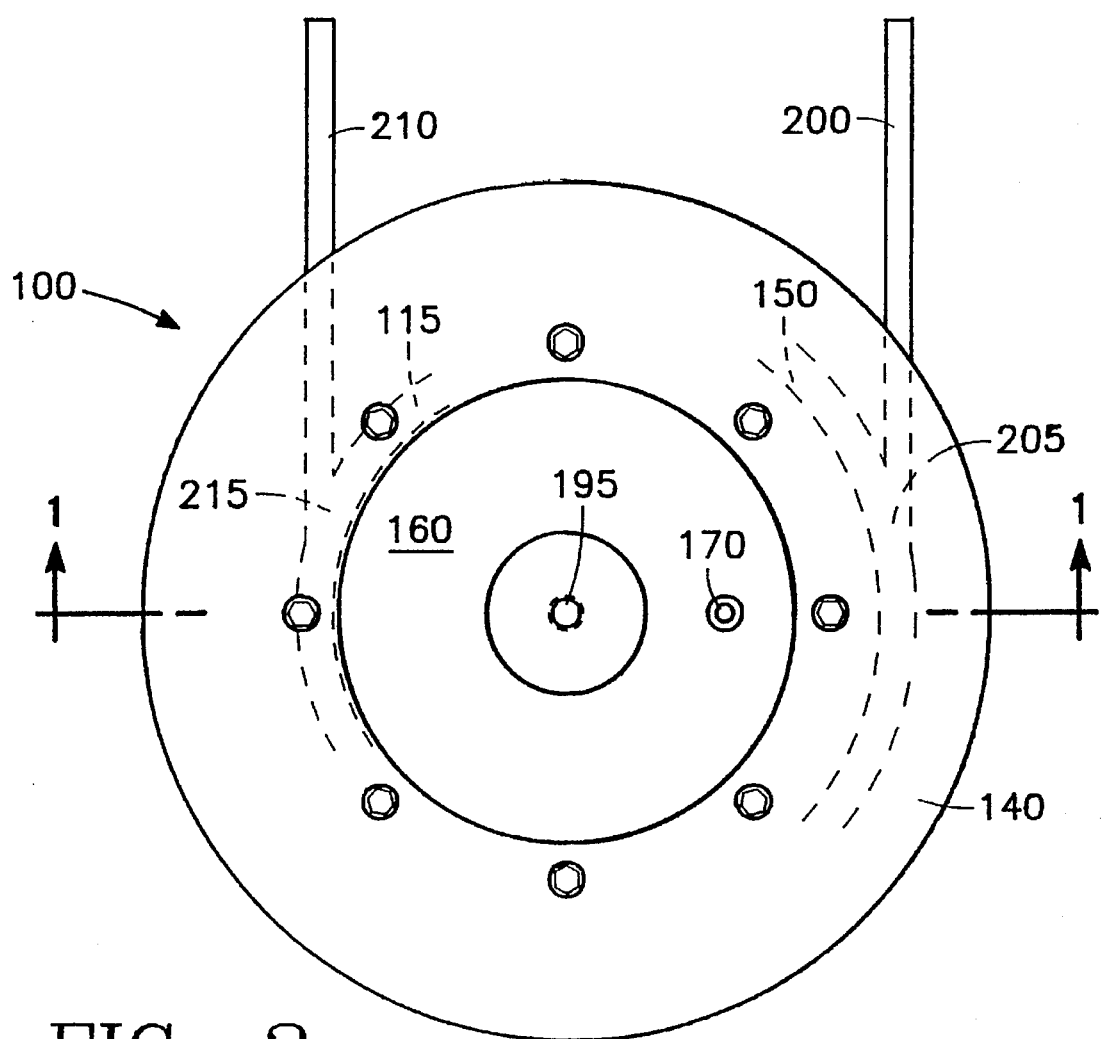
FIG. 2 is a elevation view of the analyzer of FIG. 1.

As shown in the top view of RDMA 100 in FIG. 2, a sheath flow entry tube 200 is affixed to the annular sealing cap 140 and connects at a tangential point 205 to sheath air channel 150. In a similar manner, an aerosol flow tube 210 is affixed to housing 105 and connects at a tangential point 215 to sample channel 115.

While the invention has been described with respect to an embodiment in which the sheath air channel 150 and the sample channel 115 are circular, any other suitable arcuate path, other than circular, may be employed in carrying out the invention by one skilled in the art. In addition, the sheath air channel 150 and sample channel 115 may be reversed in position, i.e., with the sheath air channel 150 in the housing 105 and the sample channel in annular sealing cap 140.

Figure 3:
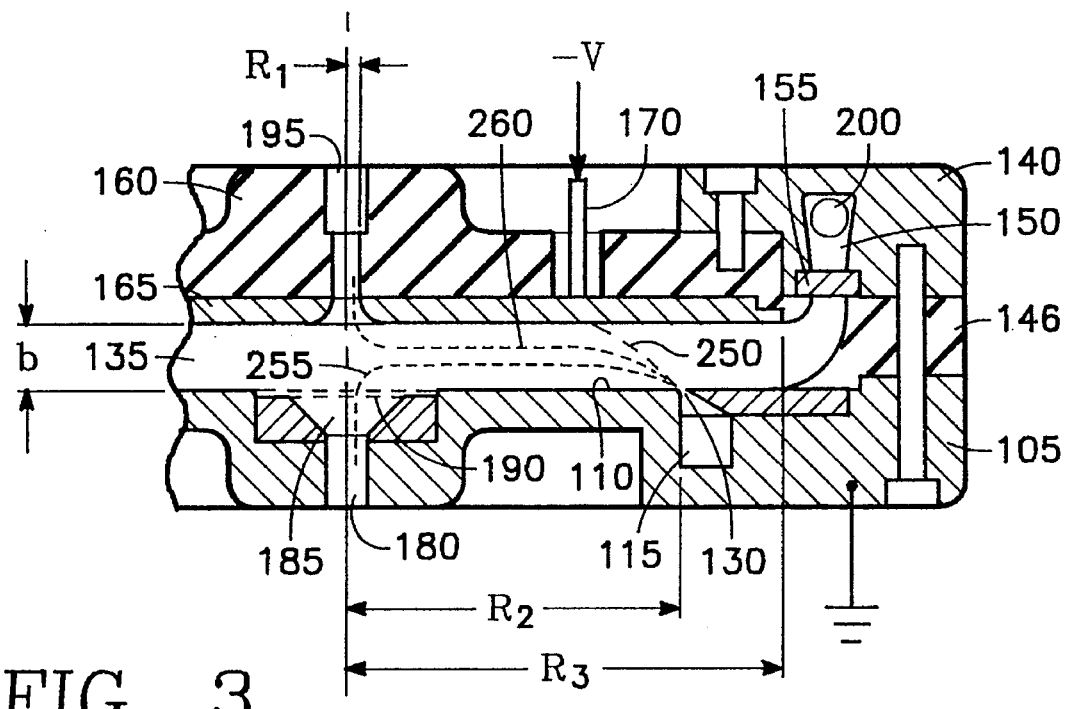
FIG. 3 is a cross section view of the analyzer of FIG. 1 showing aerosol streamlines.

The basic manner in which the RDMA classifies aerosol particles is shown in the cross section of the RDMA in FIG. 3. Particle-free sheath air enters the RDMA tangentially through a sheath flow tube 200 into the sheath air channel 150. The aerosol flow is also introduced tangentially through an aerosol flow tube 210 into the sample channel 115. The aerosol flow merges with the sheath flow within the test chamber 135 and is convected in a laminar flow toward the axis of the RDMA. The housing 105 and first circular electrode 110 are grounded and a negative high voltage is applied to the second circular electrode 165 by means of the voltage connector 170. The resulting electric field in the test chamber 135 attracts positively charged particles from the aerosol layer and causes them to migrate across the sheath air flow toward the second circular electrode 165 as the laminar flow carries them toward the axis of the RDMA. (Although classification of positively charged particles is the normal mode of operation, negatively charged particles could be classified by changing the polarity of the charge on electrode 165.) Charged particles with a relatively high mobility deposit on the second circular electrode 165 upstream of the aerosol inlet gap 130, as shown by streamline 250 in FIG. 3. Particles with a relatively low mobility are discharged with the excess flow through the excess flow outlet 180, as shown by streamline 255. Particles within a narrow range of mobility between the two can reach the sample flow outlet 195, as shown by streamline 260, and are extracted with the sample flow.

The housing 105 (shown in FIG. 1), second circular electrode 165 (shown in FIG. 1), and circular screen 190 (shown in FIG. 1) are desirably formed of stainless steel because it is an electrical conductor and has desirable corrosion resistant properties, but these components could be formed from other durable, conducting metals. The insulating disk 160 (shown in FIG. 1) is formed of any suitable insulator, such as Delrin plastic.

The size of the RDMA depends on the particle sizes to be classified. For the analysis of particles in the 3 to 200 nanometer diameter size range, the dimensions of $R_1$ (radius of the sample flow outlet 195), $R_2$ (inner radius of the sample channel 115), and $R_3$ (radius of the electrodes 110 and 165) in FIG. 3 are preferably 0.556 cm, 5.093 cm, and 6.093 cm, respectively. The separation b between electrodes is preferably 1.00 cm.

Particle size distributions are determined by making a number of measurements as the voltage applied to the RDMA is varied either incrementally or continuously. The relation between the voltage and particle size distribution can be derived from equations provided in an article coauthored by the inventors, Radial Differential Mobility Analyzer, Aerosol Science and Technology (in press). By combining equations (1) and (18) in the paper and assuming that the number or elementary charges per particle is one for sufficiently small particles, the relation between voltage applied to the RDMA of the invention and the particle size extracted from the RDMA can be expressed as follows:

$$\frac{[2Q_{sh} + Q_a - Q_s]b}{2\pi(R_2^2 - R_1^2)v} = \frac{neC(D_p)}{3\pi\mu D_p}$$

where $Q_{sh}$ is sheath flow rate, $Q_a$ is incoming aerosol flow rate, $Q_s$ is the classified sample flow rate, $R_1$ is the radius of the sample flow outlet 195 (shown in FIG. 3), $R_2$ is the inner radius of the sample flow outlet 115 (shown in FIG. 3), b is the separation between the first circular electrode 110 (shown in FIG. 3) and the second circular electrode 165 (shown in FIG. 3), and V is the voltage applied to the second circular electrode 165, e is the elementary unit of charge ($1.604 \times 10^{-19}$ coulombs), $C(D_p)$ is a coefficient known in the art as the slip correction, $\mu$ is air viscosity, $D_p$ is the particle diameter, and n is the number of charges on the particle.

Figure 4:
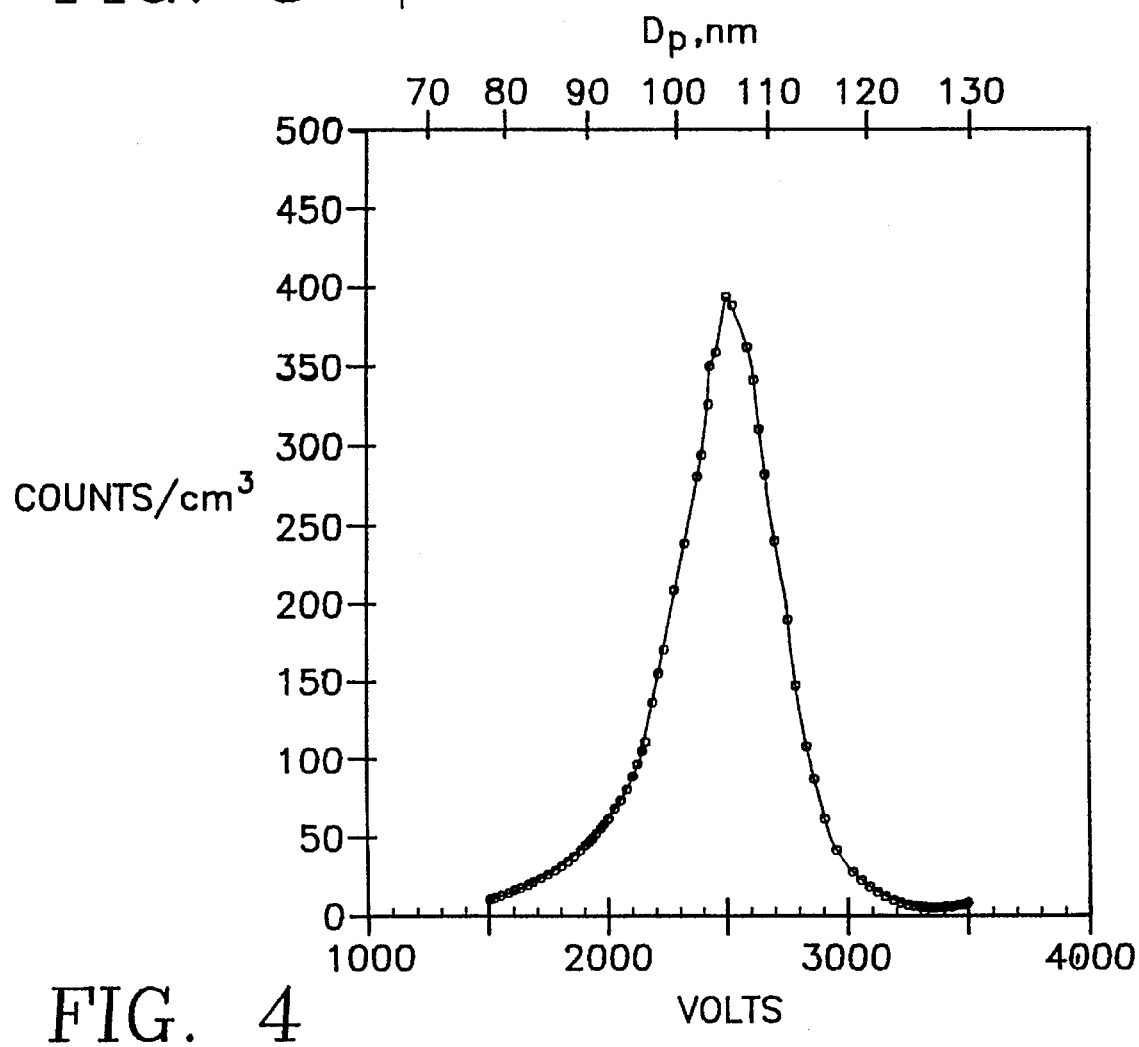
FIG. 4 is a graph illustrating aerosol particle size distribution obtained using the analyzer of FIG. 1.

Using this equation, the upper abscissa of the graph shown in FIG. 4, showing size distribution D, may be computed from the lower abscissa expressing voltage, V. The ordinate in FIG. 4 expresses the particle concentration detected in the sample flow, which can be measured by conventional means such as a condensation nucleus counter or an electrometer.

The data in FIG. 4 was obtained using polystyrene latex (PSL) spheres having a mean diameter of 105 microns (Duke Scientific Corporation, Palo Alto, Calif.). The geometric standard deviation of the particle size distribution measured with the RDMA shown in FIG. 4 was found to be 1.05, which is consistent with the certified standard deviation of the commercial PSL spheres.

Several novel features of the RDMA of the invention provide significant advantages over the prior art. As mentioned earlier, the resolution of a mobility analyzer may be defined as the ability of the analyzer to transmit particles within a narrow range of mobilities. The resolution is degraded by flow maldistributions and diffusion losses. The present RDMA overcomes resolution losses due to flow maldistributions by the use of tangential flow for sheath air entrance into the RDMA.

In addition, the use of a unique annular insert 155 (shown in FIG. 1) also reduces flow maldistributions. The insert 155 is advantageously formed of a porous material that evenly distributes the sheath flow and provides a uniform flow field. For example, the porous material is selected to provide a sufficient pressure drop to achieve a uniform sheath air velocity through the material, which distributes the flow uniformly over the annular surface. One such material is a high density polyethylene with a pore size of approximately 35 microns, such as POREX Porous Plastic sold by POREX Technologies, Fairburn, Ga.

The RDMA of this invention reduces diffusion losses to its walls by enhancing the extent of laminar flow. For example, the radial velocity of the sheath air and aerosol flows increases as the flows approaches the axis. In order to maintain laminar flow in this region, a conical excess flow outlet is used to form a large cross section for the excess flow.

The RDMA of the first embodiment also maintains a uniform electric field in the selection or sampling chamber. This feature enables better theoretical prediction of the performance of the RDMA. This embodiment achieves this result by the use of a circular conducting screen over the conical outlet port. This screen provides a constant distance between the electrodes and results in a more uniform field in the sampling chamber. The uniformity of the field is also enhanced if the radius of the electrodes is larger than the radius of the sample channel by at least the electrode spacing.

The present RDMA also achieves a higher transmission efficiency than prior mobility analyzers, especially for ultrafine particles. The transmission efficiency of a mobility analyzer may be considered as the loss of particles in the size range of interest, other than those accounted for by the transfer function. One factor reducing transmission efficiency is the loss of particles to the walls of the analyzer at the inlet and outlet due to diffusion. The RDMA of this invention reduces these losses by using tangential entry of the aerosol. In addition, losses upon exit are reduced by the use of a single, axial extraction port. The RDMA achieves a transmission efficiency of 0.85 to 0.90 in the 3 to 10 nanometer particle size range.

Finally, the RDMA of the invention provides a simple design that reduces the number of precision parts that must be fabricated below that for previous mobility analyzers, which has the advantages of a smaller, more lightweight, and lower cost instrument. For example, the use of tangential flow for the entry of sheath air greatly reduces the size and complexity of parts to be machined.

Figure 5:
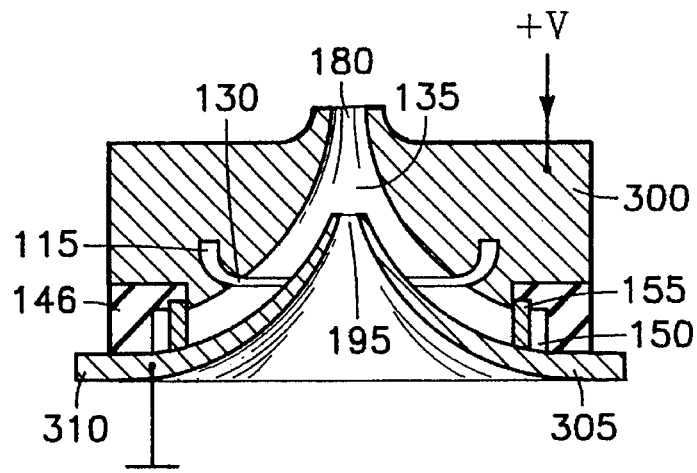
FIG. 5 is a cross section view of a second embodiment of the present invention.

Other embodiments of the invention use nonplanar electrodes for specific applications. For example, the embodiment of FIG. 5 is designed to introduce classified aerosols into a vacuum chamber. This embodiment uses the shape of a skimmer nozzle, which is the standard geometry for introduction of gas into a vacuum chamber. Many of the features of the embodiment in FIG. 5 are similar to those features in FIG. 1, and the same numbers used in FIG. 1 also designate the similar features in FIG. 5.

In the RDMA of FIG. 5, a concave electrode 300 has a generally arcuate shape in its interior portion, and is provided with a single excess flow outlet 180 at its apex that is aligned along the axis of symmetry of the sheath air channel 150 and the sample channel 115. A convex electrode 305 with a corresponding arcuate shape is provided with a single sample flow outlet 195 at its apex that is also aligned along the axis of symmetry of the sheath air channel 150 and the sample channel 115.

The aerosol sample enters the test chamber 135 at the aerosol inlet gap 130 that may be formed in the concave electrode 300, and the sheath air enters through the sheath air channel 150 and annular insert 155 that may be formed in the insulating ring 146. An annular flange 310 of the convex electrode 305 may be used to attach the RDMA to the vacuum chamber. Because the convex electrode 305 of this embodiment is designed to be attached to the exterior of a vacuum chamber, which is generally maintained at a zero electric potential, the potential difference in this embodiment is achieved by applying a positive or negative voltage potential to the concave electrode 300, to classify positively or negatively charged particles, respectively.

The concave electrode 300 and convex electrode 305 may be formed in other arcuate shapes and still achieve the pressure relieving advantage of this embodiment. For example, the arcuate shape could be formed by the rotation of a cross section of a cone, which is well known in the art to form one of a circle, parabola, ellipse, or hyperbola. In addition, the electrodes could be conical in shape as shown in FIG. 6.

Figure 6:
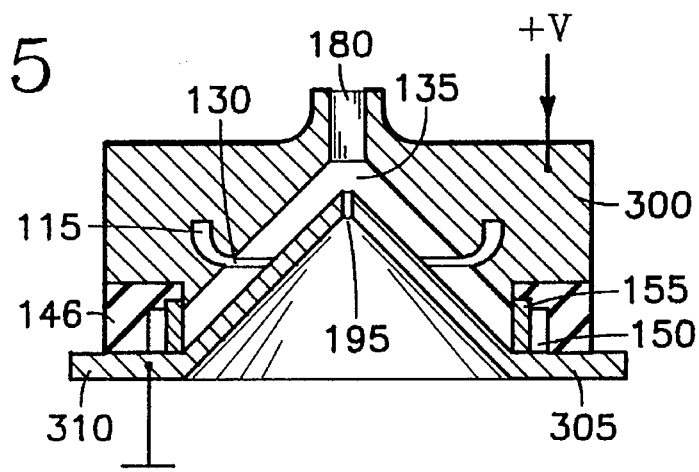
FIG. 6 is a cross section view of a third embodiment of the present invention.

By introducing classified aerosols into a vacuum, the embodiment of FIGS. 5 and 6 have many uses, such as mass spectrometer analysis. For example, such a RDMA may be used to introduce monomobility particles to be evaporated and ionized, using laser ablation techniques, for mass spectrometer analysis. The RDMA may also be used for the separation of large, gas phase ions for mass spectrometer analysis. For example, large protein particles may be charged with electrospray techniques and introduced into the RDMA for separation prior to introduction in the vacuum for spectral analysis.

Figure 7:
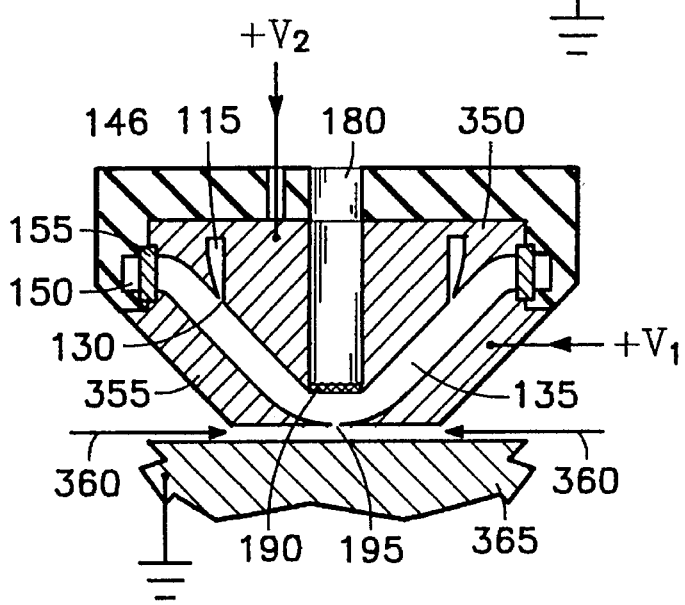
FIG. 7 is a cross section view of a fourth embodiment of the present invention.

Another embodiment of the invention is shown in FIG. 7, which is a RDMA designed for the deposition of classified particles onto a substrate, such as an integrated circuit, display device, diode laser, or other microelectronic device. In this embodiment, the sample channel 115 is formed within a second convex electrode 350 having an arcuate or conical shape. In this case, it is the second convex electrode 350 (rather than a concave electrode 300, as in FIG. 5) that is provided with a single excess flow outlet 180 at its apex that is aligned along the axis of symmetry of the sheath air channel 150 and the sample channel 115. As in the embodiment of FIG. 5, the sheath air channel 150 and insert 155 may be formed in the insulating ring 146. A second concave electrode 355 with a corresponding arcuate shape is aligned with the second convex electrode 350. A single sample flow outlet 195 is provided at the apex of convex electrode 350, along the axis of symmetry of the sheath air channel 150 and the sample channel 115.

The operation of the RDMA of FIG. 7 differs from previous embodiments because of its intended purpose. For example, it is preferable to maintain a positive gas flow 360 into this RDMA near the sample flow outlet 195 to avoid dispersion of classified particles to other regions of the deposition substrate 365. It is preferred to maintain the deposition substrate 365 at a zero electric potential to avoid electrostatic damage to the substrate. In order to classify positively charged particles, convex electrode 350 is maintained at a high positive potential, i.e, $V_2$, and concave electrode 355 is maintained at a low positive potential, i.e. $V_1$, to attract the particles through outlet 195. Conversely, in order to classify negatively charged particles, convex electrode 350 is maintained at a high negative potential and concave electrode 355 is maintained at a low negative potential.

Figure 8:
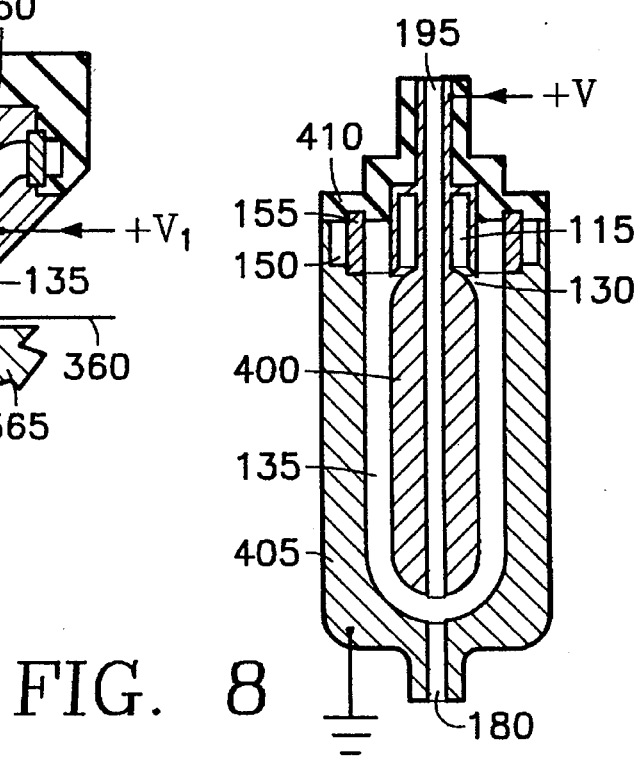
FIG. 8 is a cross section view of a fifth embodiment of the present invention.

Another embodiment of the invention is shown in FIG. 8, which is cylindrical in shape, preferably used for the classification of larger aerosol particles, i.e., generally exceeding 100 nanometers. In this embodiment, a cylindrical electrode 400 is mounted in the interior of a tubular electrode 405 by means of a insulating cap 410. The sample channel 115 is formed in the cylindrical electrode 400 and the sheath air channel 150 and insert 155 may be formed in either the insulating cap 410 (as shown) or the tubular electrode 405. Again, a single sample flow outlet 195 and single excess flow outlet 180 are provided along the axis of symmetry of the sheath air channel 150 and the sample channel 115. Since tubular electrode 405 forms the exterior of this RDMA, it is desirable to maintain tubular electrode 405 at zero potential and apply either a positive or negative voltage to the cylindrical electrode 400, to classify negatively or positively charged particles respectively.

In operation, the RDMA of FIG. 8 provides a longer path in the test chamber 135 that is necessary for larger particles to migrate from the sample channel 115 to the outlets 180 and 195 and achieve separation. The longer path is needed because larger particles migrate at a slower velocity. In general, the radial embodiments of the invention, such as those shown in FIGS. 1–3 and 5–7 achieve advantageous separation for aerosol particles of sizes from approximately 1 nanometer to a range of 100–200 nanometers. The cylindrical RDMA of FIG. 8 generally achieves advantageous separation of particles of sizes from a range of 100–200 nanometers to approximately 1 micron.

Although the present invention has been described with reference to preferred embodiments, workers skilled in the art will recognize that changes may be made in form and detail without departing from the spirit and scope of the invention.

What is claimed is:

1. A differential mobility analyzer for the classification of aerosols, comprising:

a chamber having two generally parallel faces and means to confine gases in said chamber;

one of said faces having a generally arcuate, annular sheath air channel, having an axis of symmetry;

other of said faces having a generally arcuate, annular aerosol channel having an axis of symmetry generally coincident with said axis of symmetry of said sheath air channel;

a first one of said faces having a sample flow aperture generally aligned with said axis of symmetry of said sheath air channel;

a second one of said faces having an excess flow aperture generally aligned with said axis of symmetry of said sheath air channel; and means for maintaining an electric potential difference between said faces.

2. The analyzer of claim 1 wherein said faces are generally planar.

3. The analyzer of claim 1 wherein said sheath air channel and said aerosol channel are generally circular.

4. The analyzer of claim 3 wherein said sheath air channel has a diameter greater than a diameter of said aerosol channel.

5. The analyzer of claim 3 wherein said faces are generally circular and spaced apart at a predetermined distance.

6. The analyzer of claim 5 wherein said faces have radii that are each greater than the radius of said aerosol channel by at least said predetermined distance.

7. The analyzer of claim 1 further comprising:

a annulus intermediate said chamber and said sheath air channel.

8. The analyzer of claim 7 wherein said annulus is comprised of a porous material selected to provide a uniform sheath air velocity through said material.

9. The analyzer of claim 7 wherein said annulus is comprised of a polyethylene having a pore size of approximately 35 microns.

10. The analyzer of claim 1 wherein said excess flow aperture forms a generally conical shaped channel flaring outwardly at a surface of said one of said faces adjacent said chamber.

11. The analyzer of claim 1 further comprising:

a screen engaging said excess flow aperture at one of said faces and selected to conduct electric charge and to transmit gas flow with generally no change in pressure.

12. The analyzer of claim 1 wherein said first one of said faces comprises said one of said faces having a generally arcuate, annular sheath air channel, and said second one of said faces comprises said other of said faces.

13. The analyzer of claim 1 wherein said second one of said faces comprises said one of said faces having a generally arcuate, annular sheath air channel, and said first one of said faces comprises said other of said faces.

14. The analyzer of claim 1 further comprising:

means for introducing sheath air into said sheath air channel in a tangential manner.

15. The analyzer of claim 14 wherein said means comprises a tube affixed to said sheath air channel in a tangential orientation.

16. A differential mobility analyzer for the classification of aerosols, comprising:

a generally arcuate, annular aerosol channel for the introduction of said aerosol into said analyzer, said aerosol channel having an axis of symmetry;

a first electrode provided with an excess flow aperture generally aligned with said axis of symmetry, said first electrode comprises a generally tubular shaped surface;

a second electrode parallel to, and forming a sampling cavity intermediate to, said first electrode, and provided with a sample flow aperture generally aligned with said axis of symmetry, said second electrode comprises a cylindrically shaped surface concentric with said first electrode;

a generally arcuate, annular sheath air channel for the introduction of sheath air into said analyzer, having an axis of symmetry generally aligned with said axis of symmetry of said aerosol channel; and means for maintaining an electric potential difference between said electrodes.

17. A differential mobility analyzer for the classification of aerosols, comprising:

a generally arcuate, annular aerosol channel for the introduction of said aerosol into said analyzer, said aerosol channel having an axis of symmetry;

a first electrode provided with an excess flow aperture generally aligned with said axis of symmetry;

a second electrode parallel to, and forming a sampling cavity intermediate to, said first electrode, and provided with a sample flow aperture generally aligned with said axis of symmetry;

a generally arcuate, annular sheath air channel for the introduction of sheath air into said analyzer, having an axis of symmetry generally aligned with said axis of symmetry of said aerosol channel; and means for maintaining an electric potential difference between said electrodes; and wherein said first and second electrodes are generally circular and spaced apart at a predetermined distance; and wherein said first and second electrodes have radii that are each greater than the radius of said aerosol channel by at least said predetermined distance.

18. A differential mobility analyzer for the classification of aerosols, comprising;

a generally arcuate, annular aerosol channel for the introduction of said aerosol into said analyzer, said aerosol channel having an axis of symmetry;

a first electrode provided with an excess flow aperture generally aligned with said axis of symmetry;

a second electrode parallel to, and forming a sampling cavity intermediate to, said first electrode, and provided with a sample flow aperture generally aligned with said axis of symmetry;

a generally arcuate, annular sheath air channel for the introduction of sheath air into said analyzer, having an axis of symmetry generally aligned with said axis of symmetry of said aerosol channel;

means for maintaining an electric potential difference between said electrodes; and an annulus intermediate said sheath air channel and said sampling cavity.

19. The analyzer of claim 18 wherein said annulus is comprised of a porous material selected to provide a uniform sheath air velocity through said material.

20. The analyzer of claim 18 wherein said annulus is comprised of a polyethylene having a pore size of approximately 35 microns.

21. A differential mobility analyzer for the classification of aerosols, comprising:

a generally arcuate, annular aerosol channel for the introduction of said aerosol into said analyzer, said aerosol channel having an axis of symmetry;

a first electrode provided with an excess flow aperture generally aligned with said axis of symmetry;

a second electrode parallel to, and forming a sampling cavity intermediate to, said first electrode, and provided with a sample flow aperture generally aligned with said axis of symmetry;

a generally arcuate, annular sheath air channel for the introduction of sheath air into said analyzer, having an axis of symmetry generally aligned with said axis of symmetry of said aerosol channel;

means for maintaining an electric potential difference between said electrodes; and means for introducing sheath air into said sheath air channel in a tangential manner, said introducing means comprising a tube affixed to said sheath air channel in a tangential orientation.

22. A differential mobility analyzer for the classification of aerosols, comprising:

a chamber having two planar, parallel faces and means to confine gases in said chamber;

one of said faces having a generally arcuate, annular sheath air channel;

other of said faces having a generally arcuate, annular aerosol channel generally aligned symmetrically with said sheath air channel;

a first one of said faces having a sample flow aperture generally aligned symmetrically with said sheath air channel;

a second one of said faces having an excess flow aperture generally aligned symmetrically with said sheath air channel; and means for maintaining an electric potential difference between said faces.

23. The analyzer of claim 22 wherein said sheath air channel has an axis of symmetry, and said aerosol channel has an axis of symmetry generally coincident with said axis of symmetry of said sheath air channel.

24. The analyzer of claim 22 wherein said sheath air channel and said aerosol channel are generally circular.

25. The analyzer of claim 24 wherein said sheath air channel has a diameter greater than a diameter of said aerosol channel.

26. The analyzer of claim 22 further comprising:

a planar annulus intermediate said chamber and said sheath air channel.

27. The analyzer of claim 26 wherein said annulus is comprised of a porous material selected to provide a uniform sheath air velocity through said material.

28. The analyzer of claim 26 wherein said annulus is comprised of a polyethylene having a pore size of approximately 35 microns.

29. The analyzer of claim 22 wherein said first one of said faces comprises said one of said faces having a generally arcuate, annular sheath air channel, and said second one of said faces comprises said other of said faces.

30. The analyzer of claim 22 wherein said second one of said faces comprises said one of said faces having a generally arcuate, annular sheath air channel, and said first one of said faces comprises said other of said faces.

31. The analyzer of claim 22 further comprising:

means for introducing sheath air into said sheath air channel in a tangential manner.

32. The analyzer of claim 31 wherein said means comprises a tube affixed to said sheath air channel in a tangential orientation.

* * * * *